(12) United States Patent
Werny (10) Patent No.: US 6,663,557 B2
(45) Date of Patent: Dec. 16, 2003

(54) DYNAMIC MAGNETIC DEVICE AND METHOD, AND COMPONENTS THEREOF

(76) Inventor: Scott H. Werny, 1917 Kuapapa Pl., Honolulu, HI (US) 96819

( * ) Notice: Subject to any disclaimer, the term of this patent is extended or adjusted under 35 U.S.C. 154(b) by 23 days.

(21) Appl. No.: 10/073,180

(22) Filed: Feb. 13, 2002

(65) Prior Publication Data

US 2002/0111614 A1 Aug. 15, 2002

Related U.S. Application Data

(60) Provisional application No. 60/268,050, filed on Feb. 13, 2001.

(51) Int. Cl.7 ................................................. A61N 1/00
(52) U.S. Cl. ......................................................... 600/15
(58) Field of Search ...................................... 600/9–15

(56) References Cited

U.S. PATENT DOCUMENTS

| | | |
|---|---|---|
| 4,132,061 A | 1/1979 | Mathys |
| 4,727,857 A | 3/1988 | Hörl |
| 4,846,159 A | 7/1989 | Anzai et al. |
| 5,277,692 A | 1/1994 | Ardizzone |
| 5,304,111 A | 4/1994 | Mitsuno et al. |
| 5,514,072 A | 5/1996 | Ardizzone |
| 5,538,495 A | 7/1996 | Ardizzone |
| 4,489,711 A | 1/1997 | Latzke |
| 5,632,720 A | 5/1997 | Kleitz |
| 4,549,532 A | 8/1998 | Baermann |
| 5,817,000 A | 10/1998 | Souder |
| 5,871,438 A | 2/1999 | Ardizzone |
| 6,001,055 A | 12/1999 | Souder |
| 6,126,589 A | 10/2000 | Brooks |

*Primary Examiner*—John P. Lacyk (57) ABSTRACT

A dynamic magnetic device and a method generate a dynamic magnetic field of alternating polarity when it is moved. The device has a magnetic disc with substantially an alternating polarity pattern rotatably mounted to a housing. The magnetic device is biased mounted so that when the user moves the housing, gravity or the earth's magnetic field or both causes user-relative rotational movement of a magnetic disc with an alternating polarity pattern.

22 Claims, 9 Drawing Sheets

DYNAMIC MAGNETIC DEVICE AND METHOD, AND COMPONENTS THEREOF

This application claims priority to provisional application Ser. No. 60/268,050, filed Feb. 13, 2001, and incorporates the disclosure thereof in its entirety.

BACKGROUND

Scientific communities, including medical, have conducted many studies on the effectiveness of magnet therapy, and numerous publications on this subject have been widely publicized. Magnetic fields have been used for many therapeutic treatments, including relief of pain and inflammation associated with soft tissue and musculoskeletal injuries, relief of pain from osteoarthritis and rheumatoid arthritis, relief of pain associated with postpolio syndrome, relief of headache pain, relief of pain from tendonitis, relaxation of muscles from exertion or tension, and more. In application, therapeutic magnetic sheets or pads have been designed and created with stationary alternating magnetic polarity patterns that are believed to increase blood flow and therefore, accelerate the healing of injured body parts when they are placed on or near them.

Over the years, magnetic patterns have improved, enhancing their effectiveness. Various rectangular, concentric circular, checkerboard, wave, triangular, and spiral patterns have been contemplated and are being used. Therapeutic magnetic application relies on the principles of electricity and magnetism, where the charged particles moving perpendicularly through a magnetic field experience force. Human blood carries charged particles, since it is filled with iron, ions, and electrolytes. Therefore, a blood vessel exposed to a proper alignment of alternating magnetic fields can experience sufficient force to create sufficient heat to cause a widening of the blood vessel and thus an increase in blood flow. It is also believed that extra movement of polar particles in the blood moving to align themselves to the alternating magnetic polar fields can sufficiently mix the blood to allow components of the blood to have an easier time recognizing foreign matter.

In this respect, U.S. Pat. No. 4,489,711 to Latzke; U.S. Pat. No. 4,549,532 to Baermann; U.S. Pat. No. 5,304,111 to Mitsuno et al.; U.S. Pat. Nos. 5,277,692, 5,538,495, and 5,514,072 to Ardizzone; and U.S. Pat. No. 6,126,589 to Brooks disclose some examples involving different patterns of alternating polarity on stationary pads or sheets. The disclosures of these patents are incorporated herein by reference. The sheets are typically made of magnetized material with magnetic poles arranged in an alternating pattern of north (−) and south (+) poles or polarity zones. When placed over or on an afflicted area or an area to be treated, these polarity zones have been shown to have a therapeutic effect. For example, the pad can be applied to bruises, sore muscles, and joint pain for relief to the user from such pain. The magnetic therapy can have varying degrees of effectiveness depending on the random paths of the blood vessels that pass beneath the device and how effectively the magnetic pattern exposes these blood vessels to their alternating magnetic poles.

Also known and used in the field of magnetic therapy are devices that utilize a dynamic or oscillating field of alternating magnetic polarity, as disclosed, for example, in U.S. Pat. No. 4,727,857 to Horl; U.S. Pat. No. 5,632,720 to Kleitz; U.S. Pat. Nos. 5,817,000 and 6,001,055 to Souder. These devices use electromagnetic generators to generate an oscillating electromagnetic field, or permanent magnetic pieces that, when moved, cause their magnetic fields to move, exposing the proximate area to a dynamic magnetic field. It is believed that this exposure can move electrons on a cellular level, affecting cellular functions of nerves, muscles, and other tissues, resulting in increased blood flow, the relaxation of muscle, and connective tissue, and the blocking of pain impulses.

Specifically, Horl discloses a therapeutic magnetic device that produces pulsating magnetic fields using a rotating, motor-driven substrate that has magnets mounted thereon. Kleitz discloses a motorized revolving wand with spaced and aligned magnetic units. This provides a dynamic, constantly alternating polarity field. Souder ('000 patent) discloses some of the benefits to using a dynamic or oscillating magnetic field. Souder uses a permanent magnet or electromagnet that is freely moveable or suspended inside a frame for horizontal and/or vertical movement, and relies on the magnet to be moved by inertia. The magnet is mounted to a pivoting arm inside the frame to allow for inertial movement. Souder thus discloses using inertial or other mechanical energy inputs to move the magnet relative to the frame and the user. The frame is affixed to the user or the user's clothing or can be positioned within a moving object near the user, such as a seat, a fan, a steering wheel, or other. This type of arrangement, however, requires extra space inside the housing to provide an area for the magnet to move to, creating wasted space. This not only lowers the amount of effective coverage that the device offers, but would also make the device more conspicuous. Also, the movement may not be very uniform, which could impact the consistency of results when using such a device. Souder ('055 patent) uses electric, pneumatic, spring, hydraulic, or other motors to move the permanent magnet. The magnets can be eccentrically mounted so that when they are driven by such a motor, they vibrate, creating a concurrent vibratory massaging effect.

It is believed that a dynamic magnetic field can be more effective than a static field, depending on the area of concern, the type of application, and the individual involved. Known therapeutic dynamic magnetic field devices, however, use motors to move their magnets, which are usually powered by electricity, i.e., AC current or batteries. It is inconvenient to have to look for an outlet to plug the device in wherever the user may need to travel. In many places, there is no access to an electrical outlet. Even if the user finds some outlet, the cord limits the user's mobility. All this diminishes the effectiveness of the device, since it cuts down on the likelihood that it will be used as needed. As for battery-powered devices, they are a lot more portable, but the motor and the battery take up a lot of space and can be heavy. To attach such a device with a motor and a battery to a human body is inconvenient, since it is cumbersome and conspicuous. Also, batteries will always need to be replaced or recharged. These devices can be more convenient in wand form, but to be effective, these wands have to be held by the user's hand near the body, making it difficult for the user to perform other tasks, or to move around while using the device. Again, they are conspicuous. Another consideration is that motor driven devices have motors that can malfunction or generate noise.

U.S. Pat. No. 4,846,159 to Anzai, et al. uses hand-powered rotating magnetic balls to roll and massage. These magnetic balls create an alternating magnetic field when they are rolled on the body or spun by hand. The drawback to this type of device is that it is manual, which is not convenient to user.

Therefore, there is a need to provide a therapeutic magnetic device that is secured to the user and provides the benefits of a magnetic pad with alternating poles when stationary, and provides the benefits of a dynamic alternating magnetic field when the user moves, without using a motor or manually generating the field. The present invention addresses this need.

SUMMARY OF THE INVENTION

The present invention relates to a dynamic magnetic device and a method thereof, and components thereof, namely a magnetic pad or disc and a housing thereof.

One aspect of the present invention is a dynamic magnetic device, which can include a magnetic disc and a housing. The magnetic disc has an alternating magnetic pole pattern. The housing can be configured to permanently or replaceably encase and hold the magnetic disc for rotation. The magnetic disc is configured and mounted to the housing so that the magnetic disc rotates or oscillates relative to the housing upon imparting motion to the housing to generate a dynamic or oscillating magnetic field.

The magnetic disc can be mounted to the housing with a weight imbalance, so that gravity can cause the magnetic disc to rotate. In this respect, the magnetic disc can be rotatably mounted to the housing so that the magnetic disc has an axis of rotation offset from a center of the magnetic disc. Alternatively, the mass of the magnetic disc can be unevenly distributed to create the weight imbalance, which can be made by making one area remote from a center of the magnetic disc have more mass. Alternatively, or in combination with the above, the magnetic disc can have one or more openings along one area or specific areas thereof, away from a center of the magnetic disc, to create the weight imbalance. Alternatively, or in combination with any of the above configurations, the magnetic disc can be made non-circular.

The magnetic disc can be rotatably mounted to the housing using a rotating mechanism. In one embodiment, the rotating mechanism can include an axle mounted to the housing. The magnetic disc can have an opening through which the axle extends either fully or partially, and allow the magnetic disc to rotate around the axle. In another embodiment, the axle can be rotatably journaled to the housing. Moreover, in either embodiment, the rotating mechanism can further includes at least one ball bearing assembly journaled between the axle and the magnetic disc. Adding bearing assembly can allow the magnetic disc to also rotate relative to the axle, which is also rotatably journaled to the housing. In yet another embodiment, the axle can extend from one side of the housing and journaled for rotation to the magnetic disc, which can have a through opening, a partial opening, or no opening. In this respect, a bearing assembly can be mounted to the magnetic disc, and the axle journaled to the bearing assembly.

The magnetic device can include means for rotatably mounting the magnetic device to the housing, which can encompass all of the disclosed features an all equivalents thereof.

Another aspect of the present invention is a dynamic magnetic device having the magnetic disc and housing configuration previously mentioned, and means for mounting the magnetic disc to the housing so that the magnetic disc rotates or oscillates relative to the housing upon imparting motion to the housing to generate a dynamic or oscillating magnetic field. The mounting means can encompass all of the features disclosed in this application and all equivalents thereof.

Another aspect of the present invention is a magnetic device, which can be used with the present dynamic magnetic device. The present magnetic disc has an alternating magnetic pole pattern, a dominant N pole formed at one side of the disc, and a dominant S pole formed at a diametrically opposing side of the dominant N pole. This configuration can be used with the present dynamic magnetic device to create additional movement when the disc is laid horizontally using the earth's magnetic field, or other magnetic field.

Another aspect of the present invention is a housing for replaceably and rotatably holding the magnetic disc. The housing can be configured as a sleeve, jacket, or casing into which any conventional magnetic disc with alternating magnetic pattern can be inserted and rotatably held in place. The magnetic disc can be rotatably held relative to the housing by pressure, clamping action, or friction, or use one or more features of the rotating mechanism previously mentioned. For instance, the magnetic disk can be inserted into a clam-shell type of casing, where the magnetic disc can be inserted and closed, or forced into a slotted sleeve. Opposing plates or members can be rotatably mounted to the casing or sleeve. The opposing plates or members can be biased toward each other to frictionally engage and maintain the magnetic disc in place relative to the opposing plates or members. Such a configuration allows the end user to insert and remove the magnetic disc. This gives the user the ability to use or experiment with different types of magnetic discs, i.e., ones with different magnetic patterns and field strengths.

In this respect, the housing can have first and second walls for covering the magnetic disc. The first and second walls can be configured to rotatably maintain the magnetic disc between the first and second walls so that the magnetic disc can rotate or oscillate relative to the housing upon imparting motion to the housing to generate a dynamic or oscillating magnetic field. Again, the housing can include the mounting means previously mentioned.

Another aspect of the present invention is a method of generating a dynamic magnetic field, comprising the steps of providing the previously magnetic disc and housing and rotatably mounting the disc to the housing, and moving the housing to thereby impart rotary movement to the magnetic disc to impart a dynamic or oscillating magnetic field. In this respect, the method can further include attaching the housing to a part of a person or animal so that the magnetic disc rotates to impart a dynamic or oscillating magnetic field when the person or animal moves.

BRIEF DESCRIPTION OF THE DRAWINGS

These and other features, aspects, and advantages of the present invention will become more apparent from the following description, appended claims, and accompanying exemplary embodiments shown in the drawings, which are briefly described below.

DETAILED DESCRIPTION

Figure 4:
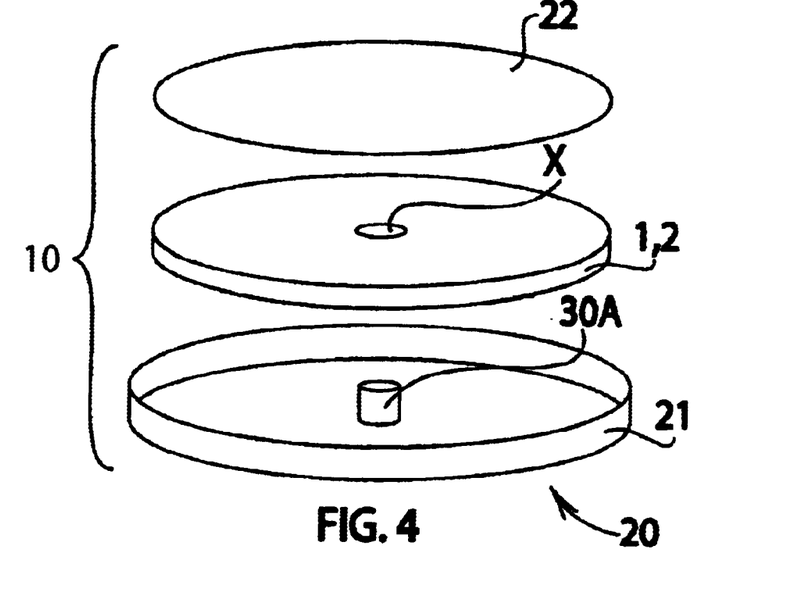
FIG. 4 is an exploded schematic view of a dynamic magnetic device according to the present invention.

FIG. 4 schematically illustrates, in an exploded view, a dynamic magnetic (DM) device 10 according to the present invention. The DM device 10 includes a housing or covering 20 and a magnetic pad or disc 1, 2 rotatably or pivotally mounted to the housing 20. In this respect, the DM device 10 can include a rotating mechanism 30 that rotatably maintains, mounts, or holds the magnetic disc 1, 2 in the housing. The magnetic disc usable with the present DM device can be any conventional disc 1, such as the one illustrated in FIG. 1, which illustrates an advanced magnetic disc 1 of the prior art having alternating north and south poles N, S., such as the one disclosed in the previously identified Ardizzone patent, the disclosure of which incorporated herein by reference.

Figure 1:
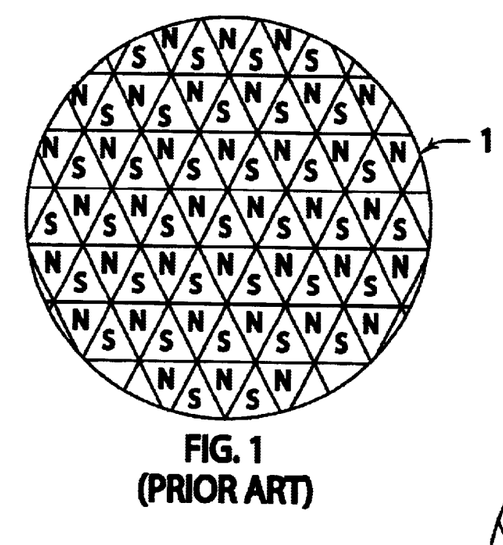
FIG. 1 schematically illustrates a magnetic disc of the prior art.
Figure 2:
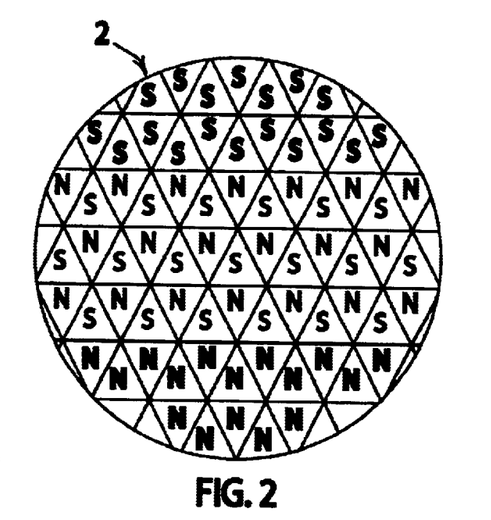
FIG. 2 schematically illustrates an embodiment of a magnetic disc according to the present invention.

The magnetic disc of course can have different magnetic configurations than shown in FIG. 1. For example, FIG. 2 shows another embodiment of a magnetic disc 2 that can be used with the present DM device 10. The embodiment of FIG. 2 is similar to the embodiment of FIG. 1, but with non-alternating opposite poles at diametrically opposite sides, i.e., as illustrated, around 11–1 and 5–7 o'clock positions. As the magnetic disc 2 has dominant N and S poles in the diametrically opposite positions, it can interact with the earth's magnetic field.

Figure 3:
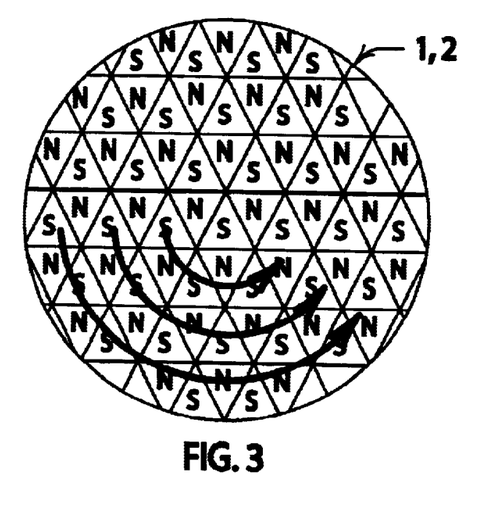
FIG. 3 schematically illustrates how the area underneath the disc is exposed to a dynamic alternating magnetic field.

FIG. 3 illustrates how the spinning or oscillating magnetic disc 1, 2 dynamically subjects the area beneath it to an alternating polar field. The applied magnetic field can vary depending on the amount, the speed, and the direction of rotation.

The magnetic disc preferably is a permanent magnet, with alternating polar fields, having a circular or substantially circular configuration, as shown in FIGS. 1, 2, and 5–11. The strength of the magnet can be made weak or strong, depending on the desired effective penetration of magnetic therapy. For the DM device application, the magnetic disc 1, 2, is preferably relatively stiff so it does not easily bend, and can have a small hole for pivotally mounting to the housing 20 at or offset from its center, such as shown respectively in FIGS. 7 and 8. The magnetic disc 1, 2 according to the present invention is designed to be pivotally mounted to the housing so that it can rotate, pivot, or oscillate relative to the housing 20.

According to the present invention, the magnet disc 1, 2 can be made to rotate or pivot about its pivot axis with the assistance of gravity, by creating a weight imbalance, or using earth's magnetic field, or both. Due to the weight imbalance, when the user moves the housing, gravity will drop the heaviest section toward the bottom, rotating the magnetic disc. The rotating momentum causes the magnetic disc to oscillate or swing like a pendulum.

Figure 5:
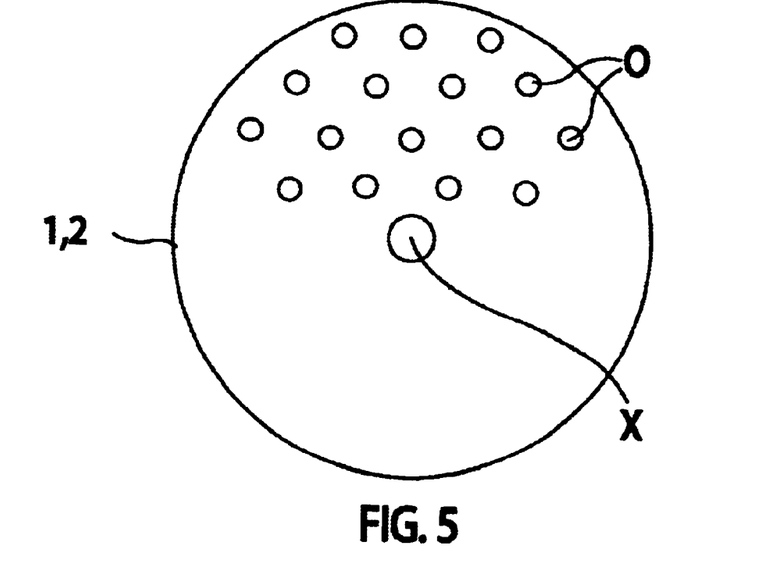
FIG. 5 illustrates one embodiment of the magnetic disc according to the present invention.
Figure 6:
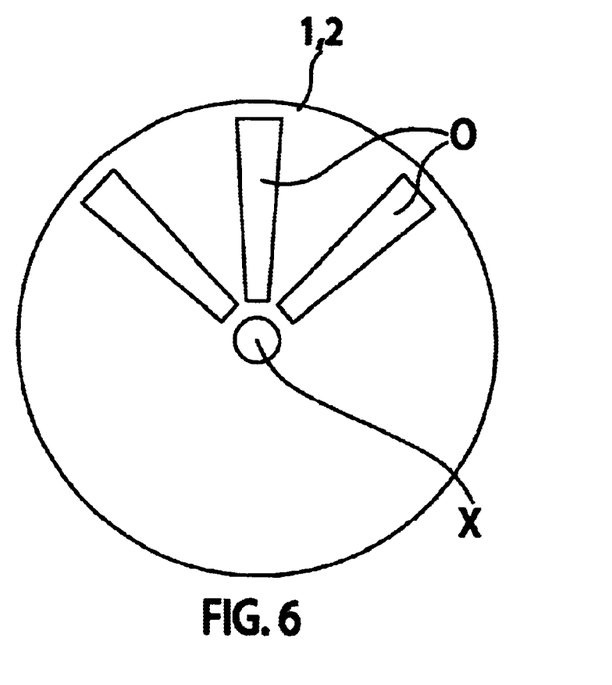
FIG. 6 illustrates another embodiment of the magnetic disc according to the present invention.

The weight imbalance can be achieved in number of ways according to the present invention, as illustrated in FIGS. 5–11. Referring to FIGS. 5 and 6, the magnetic disc 1, 2, can be circular with a uniform or even weight or mass distribution, and a central pivoting axis X. One or more openings O, such as holes, as shown in FIG. 5, and slots or cutouts, as shown in FIG. 6, can be formed along one area or specific areas thereof away from its center, to create the desired weight imbalance. The area with the openings O is lighter than the rest of the magnetic disc, creating a weight imbalance.

Figure 7:
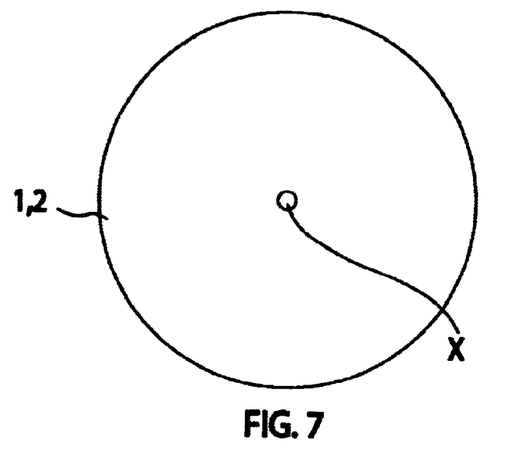
FIG. 7 illustrates another embodiment of the magnetic disc according to the present invention.
Figure 7A:
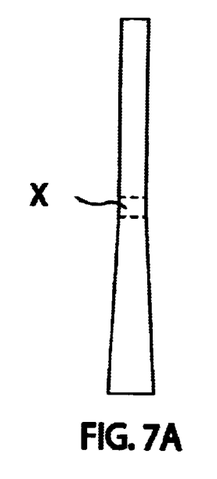
FIG. 7A is a side view of the magnetic disc of FIG. 6.
Figure 10:
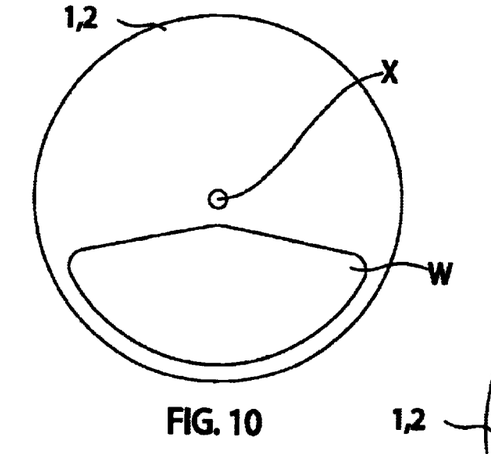
FIG. 10 illustrates another embodiment of the magnetic disc according to the present invention.
Figure 11:
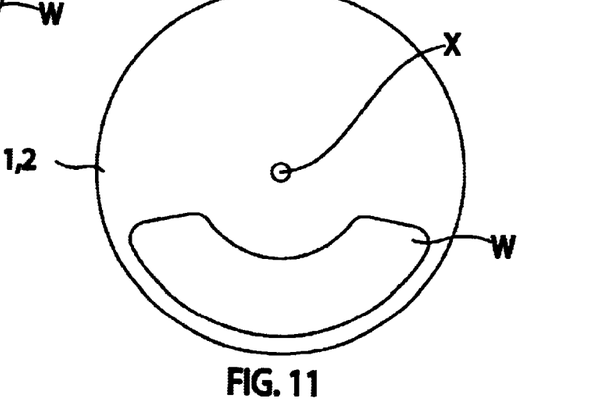
FIG. 11 illustrates another embodiment of the magnetic disc according to the present invention.

Referring to FIGS. 7, 7A, 10, and 11, another way of achieving the weight imbalance is to provide the magnetic disc with uneven weight or mass distribution, such as by making one area remote from its center heavier. This can be achieved, for example, by making one area remote from the center of the magnet disc thicker, as shown in FIGS. 7 and 7A, or attaching off-centered weights W, as shown in FIGS. 10 and 11.

Figure 8:
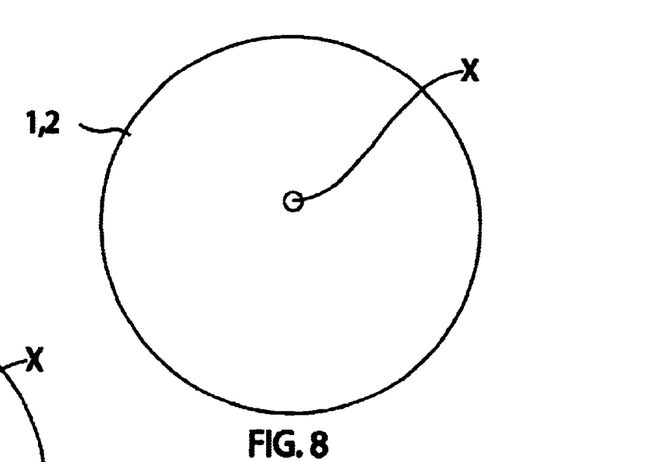
FIG. 8 illustrates another embodiment of the magnetic disc according to the present invention.
Figure 9:
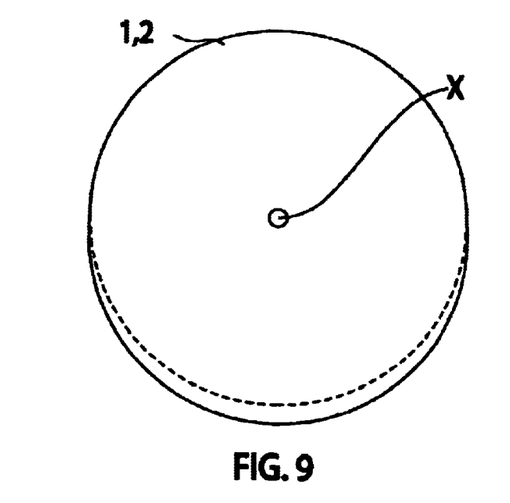
FIG. 9 illustrates another embodiment of the magnetic disc according to the present invention.

Referring to FIG. 8, another way of achieving a weight imbalance is to off-center the rotation axis by making the hole or other axle means fit through the circular magnet disc off-centered from the center of mass. Similarly, the magnet disc could be made irregularly shaped such that the center of mass is off-centered, as shown in FIG. 9.

The earth's magnetic field can be used to impart an additional movement to the magnetic disc when it is positioned horizontally or near horizontally, where gravity does not impart as significant movement to the magnetic disc. In this respect, as illustrated in FIG. 2, diametrically opposite sides of the magnetic disc 2 can have non-alternating opposite poles at diametrically opposite sides. Here, the dominant N and S poles in the diametrically opposite positions act as a compass, interacting with the earth's magnetic field to impart rotation to the magnetic disc.

The housing 20 is designed to completely enclose or encase the magnetic disc 1, 2. In this respect, although the housing 20 can have any desired configuration, it is preferable for it to be disc-shaped, complementary to the magnetic disc shape, and provided with sufficient clearance for the magnetic disc 1, 2 to freely rotate. The housing preferably is rigid so that it does not bend easily or break easily, but desirable to be as light as feasible to keep the DM device light. The housing can be made of non-metallic or non-ferrous materials, such as plastics, aluminum, brass, as some examples, which do not alter or interfere with the magnetic fields. Nonetheless, the housing can be made with some ferrous or even magnetic material for enhancing the shape of the magnetic field by focusing or spreading the magnetic field. The housing 20 preferably hermetically seals the magnetic disc and axle inside it, keeping the internal components from being affected by liquids, dirt, tampering, corrosion, removal, or loss of parts, and also allowing a lubricant to be contained therein, if desired, that will not affect the user.

Figure 12:
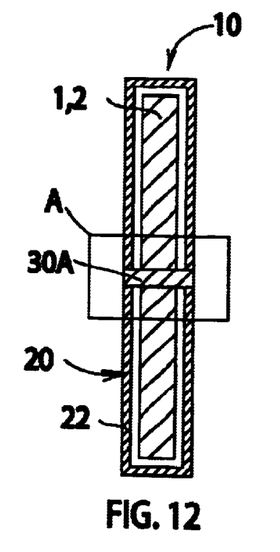
FIGS. 12–14 are cross-sectional views of the dynamic magnetic device illustrated in FIG. 4, illustrating different embodiments of the housing or covering of the dynamic magnetic device.
Figure 13:
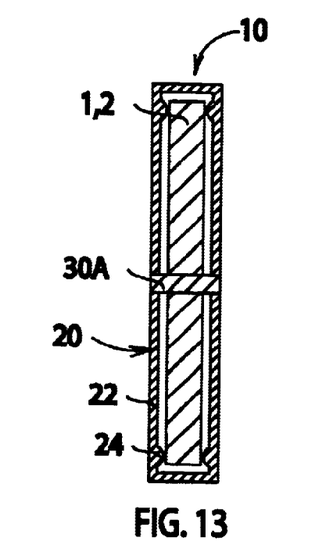
Figure 14:
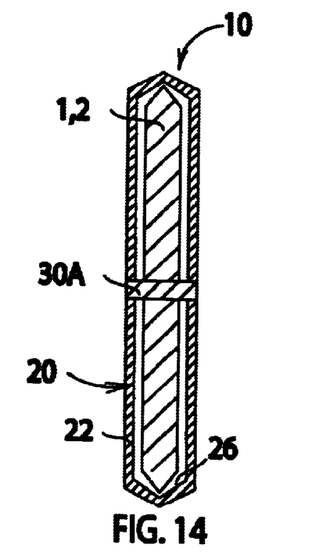

Referring to FIGS. 12–14, the housing is configured to support an axle 30A that pivotally supports the magnetic disc 1, 2. In this respect, the inside wall of the housing can have recesses or pockets 20R on the inside of the housing, in the center of each face. In the illustrated embodiments, the housing 20 can have spaced opposing pair of walls 22, which can be configured substantially parallel with each other and the magnetic disc 1, 2, and an annular portion 21 connecting the walls 22. The recesses 20R can be formed opposingly on the insides of these walls 22. The ends of the axle 30A can fit into the recesses 20R. Alternatively, these walls 22 can have opposing holes for receiving the axle 30A. That is, the axle 30A can extend through the holes.

Referring to FIGS. 13 and 14, the housing 20 can also have guides 24, 26 for keeping the disc aligned relative to the housing 20. For example, opposingly situated protuberances 24 can be formed on the inside of the walls 22 to keep the magnetic disc aligned, as shown in FIG. 13. These protuberances 24 can be situated near the periphery of the magnetic disc. Alternatively, channels 26 can be formed around the annular portion or circumferential periphery 21 of the housing 20 to guide a complementarily shaped periphery of the magnetic disc, as shown in FIG. 14. Ball bearings, or other suitable means could also be used to keep the magnetic disc aligned. The housing 20 also can be filled with liquid, such as oil of a suitable viscosity to dampen the lateral disc movement.

Figure 4A:
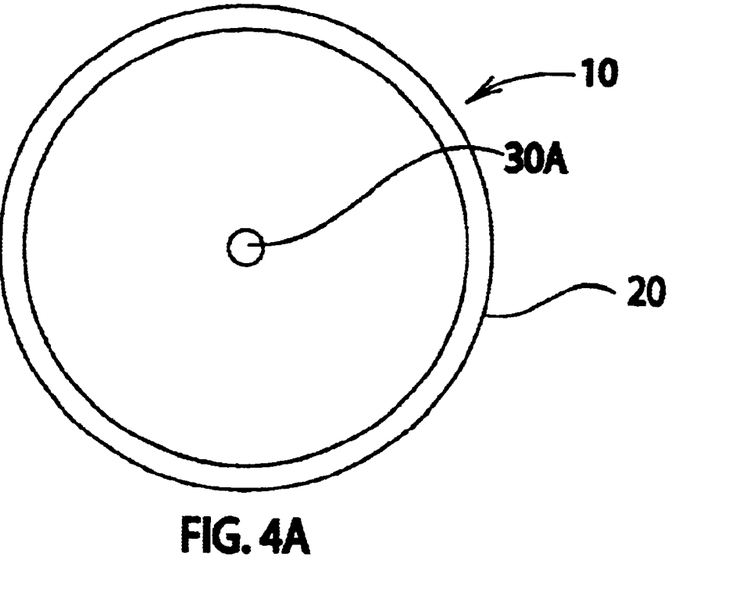
FIG. 4A illustrates one side of the housing of the dynamic magnetic device.

All or portions of the housing can be transparent, allowing the user to see the rotating magnet inside. A fabric F may be attached to the side of the housing that contacts the user, to allow heat to dispel in that area, as shown in FIG. 4A.

The housing can be attached or secured to the user's skin, or secured to the user as is commonly done by sliding it under a strap, wrap, or bandage. Alternatively, a Velcro™ device can be used.

Figure 15:
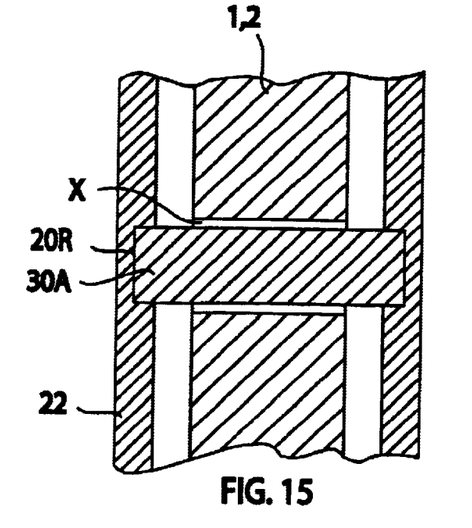
FIGS. 15–26 are views of section A of FIGS. 12–14, illustrating different embodiments of the manner in which the magnetic disc is pivotally or rotatably mounted to the housing or covering of the dynamic magnetic device.
Figure 16:
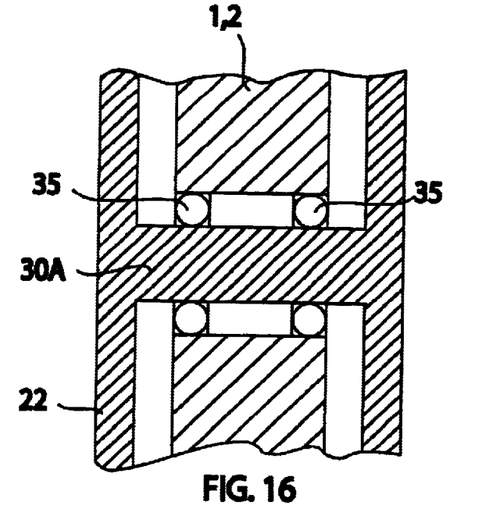
Figure 17:
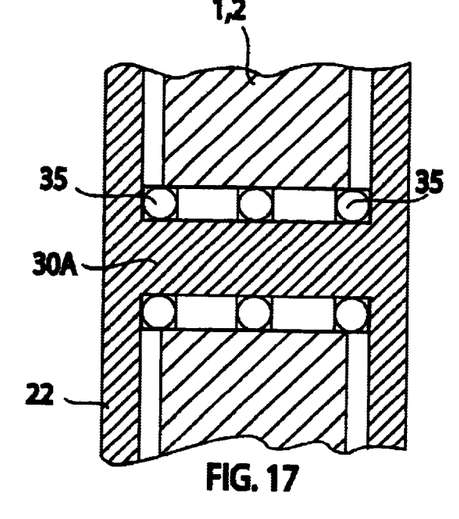
Figure 21:
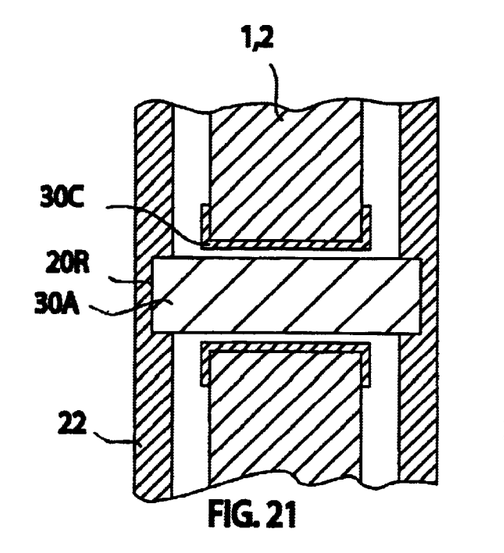
Figure 22:
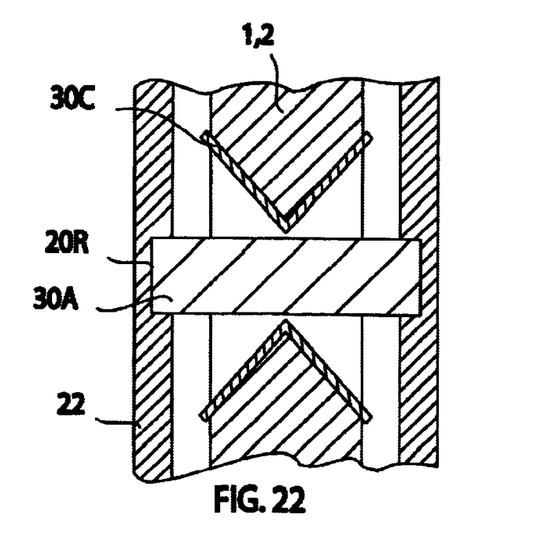

The magnetic disc 1, 2 can be rotatably mounted to the housing with the rotating mechanism 30. Referring to FIG. 15, the rotating mechanism 30, in its simplest form, comprises an axle 30A extending through the magnetic disc and secured to the housing, as previously explained. The magnetic disc 1, 2 is free to rotate around the axle 30A, like wheel. The recesses 20R formed in the housing can be cylindrical to fit a cylindrical axle end. FIGS. 21 and 22 show alternative embodiments, similar to that of FIG. 15, but include a collar 30C attached to or inserted into the disc's axle opening. The collar 30C can be made of stiffer or harder material than the magnetic disc to reduce friction from contact with the axle 30A. The axle opening itself can be chamfered so that it creates a pointed contact area for engaging the axle, or referring to FIG. 22, a hard, pointed collar can be provided. The collar 30C of FIG. 22 is similar to a knife contact, where the area contact is reduced to a line.

Figure 18:
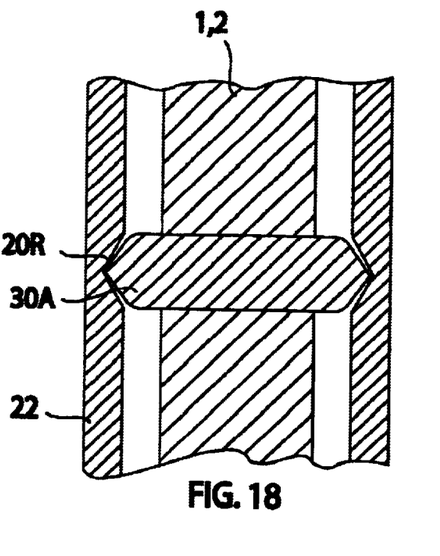
Figure 19:
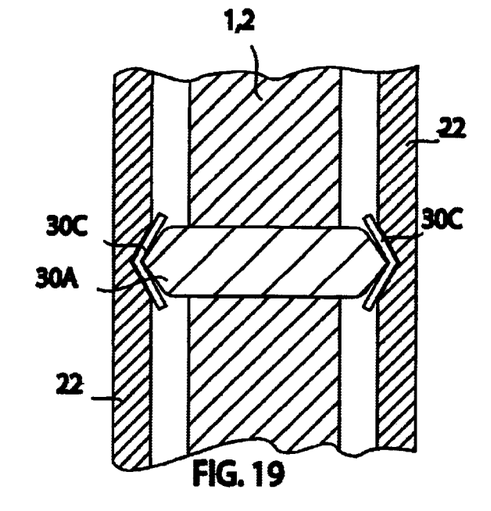
Figure 20:
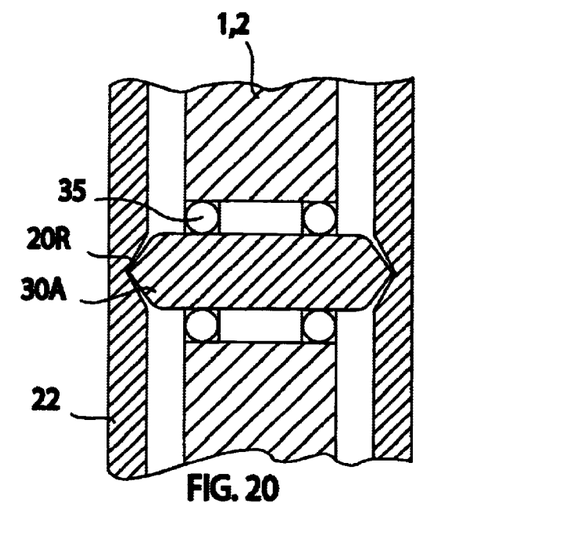

Referring to FIGS. 18 and 19, in an alternative embodiment, the axle 30A can be attached to or integral with the magnet disc so that the axle 30A spins along with the magnetic disc. Accordingly, in these embodiments, the axle 30A is journaled for rotation to the housing 20. The recesses 20R formed in the housing 20 can be cone shaped, to accommodate the cone shaped or pointed axle ends. Such pointed ends provide less friction, which allows the magnetic disc to be more sensitive to small movements. This configuration can include cone-shaped collars 30C located on the housing where the axle 30A contacts the housing 20 to further reduce friction.

The axle 30A can be configured so that the magnetic disc alone or both the magnetic disc and the axle 30A can rotate with respect to the housing 20. Simpler arrangements require less moving parts, which means there would be less chance for a malfunction and reduce manufacturing costs.

Any known axle-type mounting arrangement can be used here. The more freely the rotating mechanism allows the magnetic disc to spin, the better it operates. More complex rotating mechanisms, such as the ones that use ball bearing assemblies 35, as shown in FIGS. 16, 17, 20, 23–27, would have the advantage of providing more accurate, secure movement, which would cut down on the amount of space needed in the housing, and be more sensitive to movements.

Ideally, the magnetic disc is freely rotating so that gravity can spin it as the housing moves. In a completely level position, gravity does not have much affect on the magnetic disc. Generally, the present device is not oriented in a completely flat position for long periods. It would be possible, however to create a magnetic polarity difference on the magnetic disc that would allow the earth's magnetic field to spin the magnet in the horizontal position, aligning the magnet with the magnetic poles of the earth, much like a compass, as shown in FIG. 2. In this respect, the magnetic disc 2 illustrated in FIG. 2 has dominant N and S poles that can interact with the earth's magnetic field to cause the magnetic disc to rotate.

Figure 23:
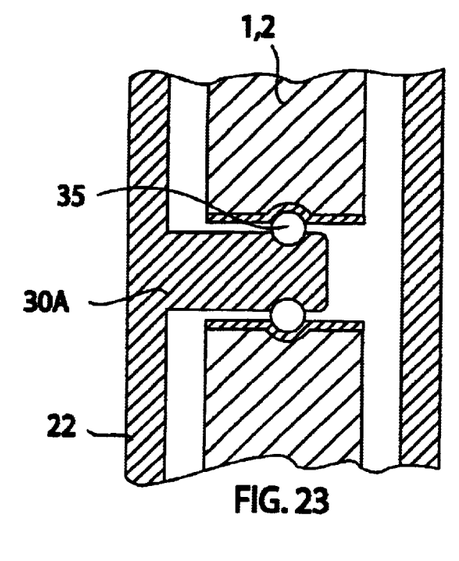
Figure 24:
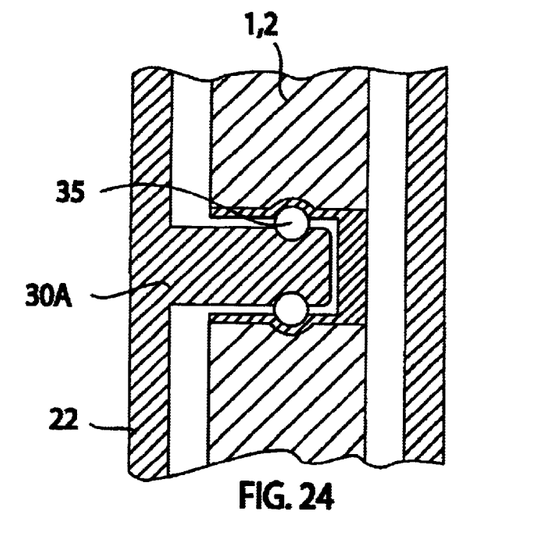
Figure 25:
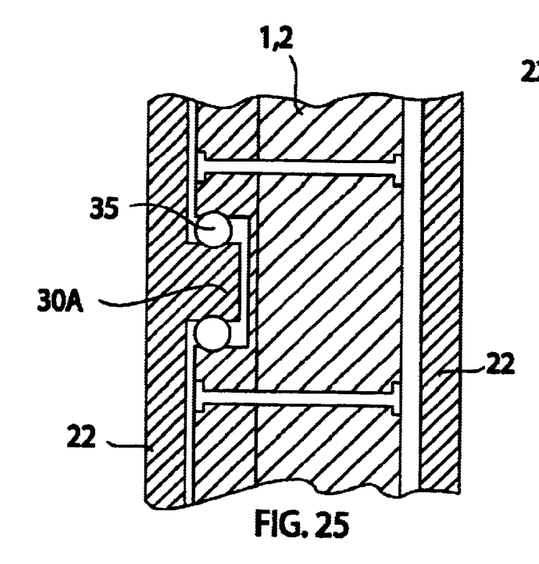
Figure 26:
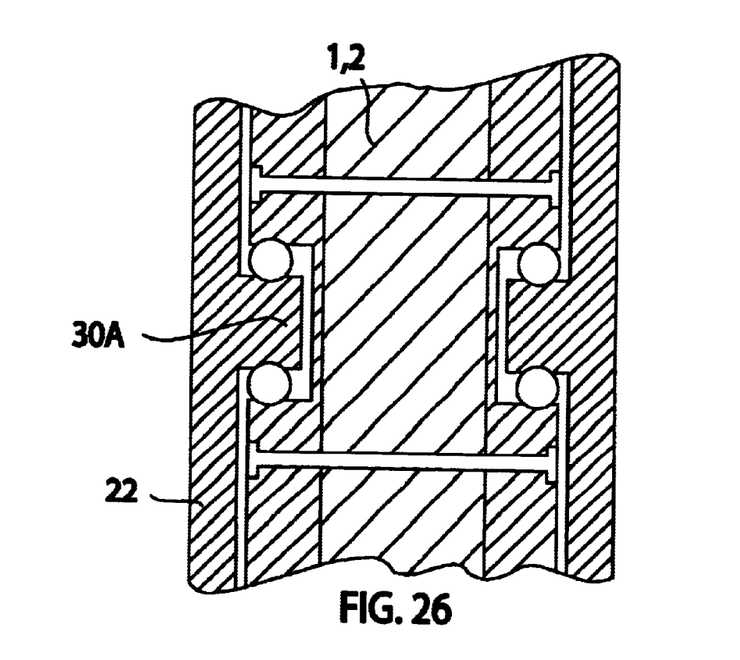
Figure 27:
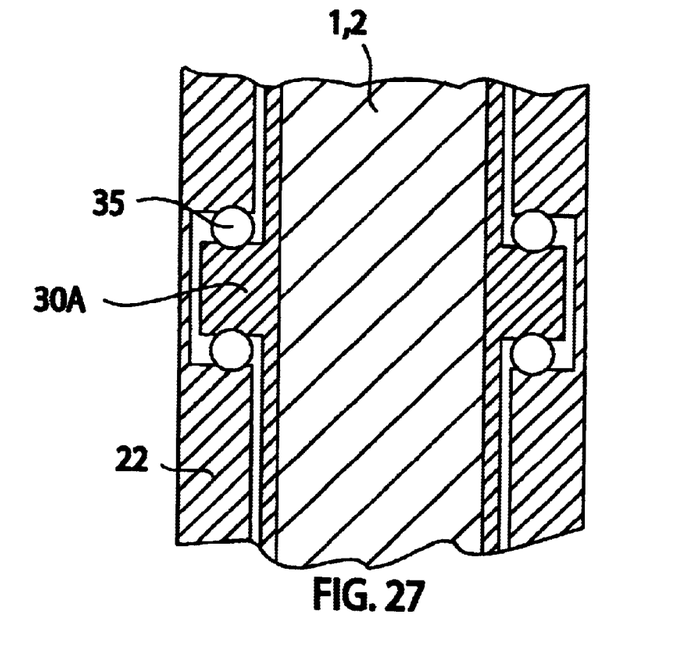
FIG. 27 illustrates an embodiment of the magnetic disc according to the present invention, which disc can be used with the dynamic magnetic device according to the present invention.

FIGS. 23 and 24 show embodiments that allow for an axle or bearing assembly 35 that only extends from one side of the housing. This configuration can reduce the thickness and the weight. The axle opening X can be a blind hole, as shown in FIG. 24, which provides more magnet area and a more uniform magnetic field. The embodiment of FIG. 25 uses a bearing assembly 35 secured to one side of the magnetic disc and journaled to one side of the housing 20 via an axle 30A. The axle 30A does not extend to the magnetic disc. Accordingly, it does not require an axle opening X. FIG. 26 shows how this same concept could be applied to both sides of the magnetic disc. Any convenient means can be used to attach the bearing assembly to the magnetic disc. Glue would be preferable since it would not require cutting into the magnetic disc, but bolts, pins, screws, staples, or an equivalent can be used. Similarly, referring to FIG. 27, ball bearing assemblies 35 can be seated into the housing walls 22. The axle 30A can be journaled to each side of the magnetic disc so that the axle extends into the bearing assembly, as shown in FIG. 27. Again the advantage here is that the magnetic disc is not cut, keeping the uniform magnetic field intact.

Another aspect of the present invention is the housing per se. The housing 20 can be configured as a sleeve, jacket, or casing into which any conventional magnetic disc with alternating magnetic pattern can be inserted and rotatably held in place. The magnetic disc can be rotatably held relative to the housing by pressure, clamping action, or friction, or use one or more features of the rotating mechanism 30 previously mentioned. For instance, the magnetic disk can be inserted into a clam-shell type of casing, where the magnetic disc can be inserted and closed, or forced into a slotted sleeve. Opposing plates or members can be rotatably mounted to the casing or sleeve. The opposing plates or members can be biased toward each other to frictionally engage and maintain the magnetic disc in place relative to the opposing plates or members. Such a configuration allows the end user to insert and remove the magnetic disc. This gives the user the ability to use or experiment with different types of magnetic discs, i.e., ones with different magnetic patterns and field strengths. Moreover, any of the embodiments illustrated here can function as a replaceable magnetic disc holder that would allow the end user to insert and remove any magnetic disc. For example, referring to FIG. 4, one of the side walls 22 can be removably or detachably attached to the annular portion 21 of the housing 20 that can be popped open or removed by the end user. After seating the magnetic disc inside the remaining housing portion (the part with the annular portion 21), the user can close the opened side with the one side wall 22. Closing the opened side applies pressure against the magnetic disc and maintains the disc in place with the rotating mechanism. In the simplest form, as illustrated in FIG. 4, the magnetic disc with the opening X can be seated on the remaining housing portion 21, 22, with the axle extending through the opening X. Thereafter, the one side wall can close the housing part 21, 22. To ensure proper alignment, the axle can be made to fully extend into an axle opening formed on the one side wall. See FIG. 4A.

It would also be possible to include a spring-type mechanism for storing some of the rotational energy induced by the user's movement and harness it back to rotate the magnetic disc when the user has stopped moving. Details for this type of mechanism can be found in self-winding watch mechanisms, which use tiny ratchet wheel arrangements that wind a spring, which in turn release to keep the watch ticking. In this case, the spring could power the rotation of the magnetic disc once the user has stopped moving. The necessary mechanisms would be small, like a watch and could be located within the housing, adjacent to the disc, or even externally of the housing. An adjustment mechanism could be added to control the speed of rotation to achieve the desired therapeutic effect.

The present DM device 10 is a significant unobvious improvement over the known dynamic magnetic device, and many distinct advantages. The present DM device can rotate its magnetic disc to impart a dynamic magnetic field without any motor. It draws energy from gravity or earth's magnetic field, and the user's movement. Since the magnetic disc has an alternating pole pattern, it is beneficial to the user even when it is not moving. Movement by the user imparts movement to the magnetic disc, and even small rotations of the disc can expose the entire underlying area to a dynamic magnetic field, giving the benefits of a dynamic or oscillating alternating magnetic field when the user moves.

Given the disclosure of the present invention, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

I claim:

1. A dynamic magnetic device comprising:
   a magnetic disc having an alternating magnetic pole pattern; and
   a housing configured to encase and hold the magnetic disc for rotation,
   wherein the magnetic disc is configured and mounted to the housing so that the magnetic disc freely rotates or oscillates relative to the housing upon imparting motion to the housing to generate a dynamic or oscillating magnetic field.

2. A dynamic magnetic device comprising:
   a magnetic disc having an alternating magnetic pole pattern; and
   a housing configured to encase and hold the magnetic disc for rotation,
   wherein the magnetic disc is configured and mounted to the housing so that the magnetic disc rotates or oscillates relative to the housing upon imparting motion to the housing to generate a dynamic or oscillating magnetic field.
   wherein the magnetic disc is mounted to the housing with a weight imbalance, so that gravity causes the magnetic disc to oscillate.

3. A dynamic magnetic device according to claim 2, wherein the magnetic disc is rotatably mounted to the housing so that the magnetic disc has an axis of rotation offset from a center of the magnetic disc.

4. A dynamic magnetic device according to claim 2, wherein the mass of the magnetic disc is unevenly distributed to create the weight imbalance.

5. A dynamic magnetic device according to claim 4, wherein one area remote from a center of the magnetic disc has more mass.

6. A dynamic magnetic device according to claim 4, wherein the magnetic disc has one or more openings along one area or specific areas thereof, away from a center of the magnetic disc, to create the weight imbalance.

7. A dynamic magnetic device according to claim 4, wherein the magnetic disc is non-circular.

8. A dynamic magnetic device according to claim 3, wherein the magnetic disc is rotatably mounted to the housing using a rotating mechanism.

9. A dynamic magnetic device according to claim 8, wherein the rotating mechanism comprises an axle mounted to the housing, and the magnetic disc has an opening through which the axle extends and allows the magnetic disc to rotate around the axle.

10. A dynamic magnetic device according to claim 9, wherein the rotating mechanism further includes at least one ball bearing assembly journaled between the axle and the magnetic disc.

11. A dynamic magnetic device according to claim 8, wherein the rotating mechanism comprises an axle mounted to the housing, and rotatably journaled to the housing.

12. A dynamic magnetic device according to claim 11, wherein the rotating mechanism further includes at least one ball bearing assembly journaled between the axle and the magnetic disc to allow the magnetic disc to also rotate relative to the axle.

13. A dynamic magnetic device according to claim 8, wherein the rotating mechanism comprises an axle extending from one side of the housing and journaled for rotation to the magnetic disc.

14. A dynamic magnetic device according to claim 13, wherein the rotating mechanism further includes at least one bearing assembly mounted to the magnetic disc, the axle being journaled to the bearing assembly.

15. A dynamic magnetic device according to claim 1, further including means for rotatably mounting the magnetic device to the housing.

16. A dynamic magnetic device according to claim 1, wherein the magnetic disc has non-alternating opposite poles at diametrically opposing sides thereof to form dominant N and S poles in the diametrically opposing sides.

17. A dynamic magnetic device comprising:
   a magnetic disc having an alternating magnetic pole pattern;
   a housing configured to encase and hold the magnetic disc for rotation; and
   means for mounting the magnetic disc to the housing so that the magnetic disc freely rotates or oscillates relative to the housing upon imparting motion to the housing to generate a dynamic or oscillating magnetic field.

18. A magnetic disc comprising:

a disc having an alternating magnetic pole pattern;

a dominant N pole formed at one side of the disc; and a dominant S pole formed at a diametrically opposing side of the dominant N poles, wherein the disc has an axis of rotation, and wherein the axis of rotation is offset from a center of the disc or the disc has an imbalanced weight distribution about the axis of rotation.

19. A housing for a dynamic magnetic device that has a magnetic disc with an alternating magnetic pole pattern, the housing comprising:

first and second walls for covering the magnetic disc, wherein the first and second walls are adapted to rotatably maintain the magnetic disc between the first and second walls so that the magnetic disc is adapted to freely rotates or oscillates relative to the housing upon imparting motion to the housing to generate a dynamic or oscillating magnetic field.

20. A housing according to claim 19, further including means for mounting the magnetic disc to the housing so that the magnetic disc rotates or oscillates relative to the housing upon imparting motion to the housing to generate a dynamic or oscillating magnetic field.

21. A method of generating a dynamic magnetic field, comprising the steps of:

providing a magnetic disc with an alternating magnetic pole pattern;

providing a housing configured to encase and hold the magnetic disc;

freely rotatably mounting the magnetic disc to the housing; and moving the housing to thereby impart rotary or oscillatory movement to the magnetic disc to impart a dynamic or oscillating magnetic field.

22. A method of generating a dynamic magnetic field, comprising the steps of:

providing a magnetic disc with an alternating magnetic pole pattern;

providing a housing configured to encase and hold the magnetic disc;

rotatably mounting the magnetic disc to the housing;

moving the housing to thereby impart rotary movement to the magnetic disc to impart a dynamic or oscillating magnetic field; and attaching the housing to a part of a person or animal, wherein the magnetic disc rotates or oscillates to impart a dynamic or oscillating magnetic field when the person or animal moves.

* * * * *